US011141239B2

(12) United States Patent
Erdmann et al.

(10) Patent No.: US 11,141,239 B2
(45) Date of Patent: Oct. 12, 2021

(54) REPROCESSING APPARATUS AND METHOD FOR OPERATING A REPROCESSING APPARATUS FOR CLEANING AND/OR DISINFECTING A MEDICAL INSTRUMENT

(71) Applicant: OLYMPUS WINTER & IBE GMBH, Hamburg (DE)

(72) Inventors: Niklas Erdmann, Hamburg (DE); Sascha Eschborn, Ahrensburg (DE); Antonia Weis, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 14 days.

(21) Appl. No.: 16/541,545

(22) Filed: Aug. 15, 2019

(65) Prior Publication Data
US 2019/0365500 A1 Dec. 5, 2019

Related U.S. Application Data

(63) Continuation of application No. PCT/EP2018/052880, filed on Feb. 6, 2018.

(30) Foreign Application Priority Data

Feb. 22, 2017 (DE) .......................... 102017202869.6

(51) Int. Cl.
*A61B 90/70* (2016.01)
*G06T 7/262* (2017.01)
(Continued)

(52) U.S. Cl.
CPC ............ *A61B 90/70* (2016.02); *B08B 9/0325* (2013.01); *B08B 9/0328* (2013.01); *G06T 7/262* (2017.01);
(Continued)

(58) Field of Classification Search
None
See application file for complete search history.

(56) References Cited

U.S. PATENT DOCUMENTS

| 4,487,075 A | 12/1984 | Karidis |
| 2006/0044548 A1 | 3/2006 | Lee et al. |

(Continued)

FOREIGN PATENT DOCUMENTS

| DE | 102013202540 A1 | 8/2014 |
| WO | WO 2011/149539 A1 | 12/2011 |

OTHER PUBLICATIONS

International Search Report dated May 29, 2018 issued in PCT/EP2018/052880, 4 pages.

*Primary Examiner* — Eric W Golightly
(74) *Attorney, Agent, or Firm* — Scully, Scott, Murphy & Presser, P.C.

(57) ABSTRACT

A reprocessing apparatus for cleaning and/or disinfecting a medical instrument including a fluid container for a reprocessing fluid and a reprocessing device. The reprocessing device includes: a reprocessing space in which the medical instrument is introduced for reprocessing; a fluid line for connection to at least one channel of the medical instrument, wherein the fluid line is configured to transport the reprocessing fluid to the at least one channel; a bubble introducing apparatus for introducing gas bubbles into the fluid line; and a gas bubble speed determining apparatus for determining a speed of the gas bubbles in the fluid line. The gas bubble speed determining apparatus includes a camera for capturing successive images of at least a portion of the gas bubbles in the fluid line.

9 Claims, 2 Drawing Sheets

(51) Int. Cl.
*B08B 9/032* (2006.01)
*A61B 1/12* (2006.01)
(52) U.S. Cl.
CPC ......... *A61B 1/125* (2013.01); *A61B 2090/701* (2016.02); *A61B 2090/702* (2016.02); *B08B 2209/032* (2013.01); *G06T 2207/10048* (2013.01)

(56) References Cited

U.S. PATENT DOCUMENTS

| | | |
|---|---|---|
| 2009/0050809 A1 | 2/2009 | Holec |
| 2009/0234595 A1 | 9/2009 | Okcay et al. |
| 2010/0078047 A1 | 4/2010 | Labib et al. |
| 2011/0097248 A1 | 4/2011 | Tomita et al. |
| 2012/0019807 A1 | 1/2012 | Brouwer |
| 2012/0227761 A1 | 9/2012 | Leighton et al. |
| 2014/0147013 A1* | 5/2014 | Shandas ............... A61B 8/5246 382/107 |

* cited by examiner

REPROCESSING APPARATUS AND METHOD FOR OPERATING A REPROCESSING APPARATUS FOR CLEANING AND/OR DISINFECTING A MEDICAL INSTRUMENT

CROSS-REFERENCE TO RELATED APPLICATION

The present application is a continuation of PCT/EP2018/052880 filed on Feb. 6, 2018, which is based upon and claims the benefit to DE 10 2017 202 869.6 filed on Feb. 22, 2017, the entire contents of each of which are incorporated herein by reference.

BACKGROUND

Field

The present disclosure relates to a method for operating a reprocessing apparatus for cleaning and/or disinfecting a medical instrument which has at least one channel, wherein a fluid line is provided, which is or will be connected to the at least one channel.

The present disclosure further relates to a reprocessing apparatus for cleaning and/or disinfecting medical instruments, having a fluid container for a reprocessing fluid and a reprocessing device, wherein the reprocessing device has a reprocessing space, in which a medical instrument can be or is introduced for reprocessing, wherein at least one channel of the medical instrument can be connected to a fluid line, wherein the fluid line serves to transport the reprocessing fluid to the at least one channel.

Prior Art

The reprocessing of medical instruments which comprise channels, for example endoscopes, both flexible and rigid endoscopes, is subdivided into the reprocessing of the external faces and the reprocessing of the internal channels or respectively channels. The reprocessing of the channels can be problematic in terms of the resulting hygiene, as it is not possible to visually inspect said channels. To this end, hoses or fluid lines are, for example, partially joined with adapters to the connections of the medical instrument or respectively of the endoscope, and a reprocessing fluid is conducted under pressure via these hoses through the internal channels or respectively channels of the endoscope, in order to clean and disinfect said channels. Problems can occur if the adapters have not been joined or have been joined incorrectly. In addition, one or more channels of the endoscope or respectively of the medical instrument can be blocked such that no fluid or too little fluid can flow through the respective channel and, therefore, the reprocessing result cannot be guaranteed.

It is therefore known from the prior art to measure a volume flow which flows through the individual channels of a medical instrument and aligning it with a reference volume flow. This can take place in the case of a reprocessing apparatus which is manufactured by the applicant and goes by the name of ETD3/4 by way of measuring the speed of ions in the fluid or by way of measuring the channel pressure, for example in the applicant's ETD Double. The volume flow can also be calculated by way of the channel pressure, resulting in the adaptation and the universality of the respective channel being verified.

Problems can occur during the determination of the speed of ions in the process fluid if a process stage is to be performed, in which no chemical components are allowed to be added to clean, for example fully desalinated, water. Determining the flow speed by way of the provision of an appropriate pressure in the channel is a relatively time-consuming process.

SUMMARY

It is an object to provide an inexpensive, efficient and less time-consuming method for operating a reprocessing apparatus for cleaning and/or disinfecting a medical instrument, and an appropriate inexpensive and efficient reprocessing apparatus as well as an appropriate module for use in a reprocessing apparatus for cleaning and/or disinfecting medical instruments.

Such object can be achieved by a method for operating a reprocessing apparatus for cleaning and/or disinfecting a medical instrument which has at least one channel, wherein a fluid line is provided, which is configured to be connected to the at least one channel, wherein, in order to determine the volume flow of a liquid flowing in the fluid line, gas bubbles are admitted into the liquid and the speed of the gas bubbles is determined and the volume flow is extrapolated on the basis of the speed of the gas bubbles.

As a result, an efficient flow control is made possible and, in addition, it is possible to check for an obstruction in a channel of the medical instrument. As a result of using gas bubbles which are introduced into the liquid, residues from other materials which are admitted into the liquid according to the prior art are prevented from remaining in the medical instrument. The gas bubbles can be consequently used as a kind of marker in order to apply a so-called particle image velocimetry method. During this, the marker particles introduced in a fluid can be acquired, such as with a camera, and evaluated in consecutive images. In order to introduce gas bubbles, such as air bubbles, a compressed air supply, a pressure cylinder or a pump can be used. Another gas, such as an inert gas, can also be introduced into the fluid line from a pressure cylinder, interposing a metering valve.

The speed of the gas bubbles can be determined by way of a processing of at least two successively captured images of a section of the fluid line.

Light, such as infrared light, can be additionally shone onto the gas bubbles, in order to increase the contrast. As a result, the gas bubbles which are used as markers in the captured images are highlighted or respectively the contrast of said markers is increased. To this end, a light direction can be provided, which is approximately parallel or antiparallel to the flow direction of the liquid. An angle of incidence of the light rays can be provided, which is between 1° and 30°, such as between 2° and 15° and, such as, between 5° and 10° to the flow direction of the liquid or respectively to a central axis of the fluid line. By using infrared light, the gas bubbles in captured images appear to be virtually white, since gas bubbles disperse the light in all directions, whereas other objects in the image only break up the light and, as a result, do not reflect in the direction of a camera.

The camera which can also be referred to as an image sensor or an acquisition apparatus, can be sensitive to various frequencies, such as, infrared sensitivity and/or sensitivity to visible light or respectively the possibility of capturing visible light exist(s).

The speed of the gas bubbles can be determined in the vicinity of a wall of the fluid line, wherein, to this end, the speed of the gas bubbles can be determined at a distance of the middle of the fluid line from a wall, wherein the distance is $\geq$(greater than or equal to) $R/2^{1/2}$, wherein R is the internal radius of the fluid line or a distance of a central axis from a wall of the fluid line. $R/2^{1/2}$ corresponds to $$\frac{R}{\sqrt{2}}.$$

In order to determine the speed, a fast Fourier transform of the successively captured images can be performed, wherein a movement vector of the gas bubbles can be established by way of a phase correlation. During this, the speed of the gas bubbles or respectively marker particles in the fluid can be derived by way of a phase correlation algorithm in the Fourier space from two or more successive images. The volume flow can then be arithmetically deduced by way of the speed of the gas bubbles. A distinction can be made between a laminar and a turbulent flow. In addition, the position of the gas bubbles in the hose can be specified or measured relative to the hose middle or respectively to the wall.

An appropriate method can be performed at each fluid line connection of a reprocessing device or with each fluid line, and with one camera in each case. However, a camera can also be used for multiple measuring points, wherein the camera can then acquire multiple measuring ranges or respectively portions of various fluid lines or the camera can be directed correspondingly towards the respective fluid lines.

A measuring error of 10% and less was attained for determining volume flows in a range of 500 ml/min to 2,900 ml/min. The method can also function at lower volume flows of, for example, 350 ml/min.

Such object can be additionally achieved by a reprocessing apparatus for cleaning and/or disinfecting medical instruments, having a fluid container for a reprocessing fluid and a reprocessing device, wherein the reprocessing device has a reprocessing space configured to accept a medical instrument for reprocessing, wherein at least one channel of the medical instrument is configured to be connected to a fluid line, wherein the fluid line serves to transport the reprocessing fluid to at least one channel, wherein a bubble introducing apparatus is provided, by means of which gas bubbles are introduced into the fluid line, wherein a gas bubble speed determining apparatus is in addition provided. As a result, a very inexpensive and safe reprocessing apparatus for cleaning and/or disinfecting medical instruments can be provided.

The reprocessing apparatus can have an adapter apparatus, to which a fluid line can be joined and which is configured to conduct the fluid to the at least one channel. If there are multiple channels in the medical instrument, the adapter apparatus can also be configured to distribute fluid among the channels.

The gas bubble speed determining apparatus can have a camera for capturing successive images of at least a portion of the fluid line.

The fluid line can be transparent in the portion, as a result of which it is possible for the camera to be arranged outside the fluid line. In particular, the portion is transparent inasmuch as the latter is transparent to visible light or to infrared light or to ultraviolet radiation. The term "transparent" also denotes a slight milkiness, wherein it is essential that the gas bubbles are still easily discernible. The camera can be configured to detect visible light, infrared light or ultraviolet light.

The gas bubble speed determining apparatus can have an illumination apparatus, wherein the illumination apparatus emits light in the infrared range in particular.

The illumination apparatus can shine light into the fluid line approximately parallel or antiparallel to a central axis of the fluid line. As a result, the contrast of the gas bubbles in the fluid can be considerably increased for the images to be captured by the camera. The portion can comprise at least one region which is $\geq R/2^{1/2}$ distant from a central axis of the fluid line, wherein R is a radius of the fluid line or a distance of the central axis from a wall of the fluid line.

The volume flow of the liquid in the fluid line can be determined in a secure manner if the gas bubble speed determining apparatus comprises a computer system, on which a fast Fourier transform of successively captured images can be performed, wherein a movement vector of the gas bubbles can be established by way of a phase correlation.

Gas bubbles can be used in order to determine the volume flow of a reprocessing fluid in a channel of a medical instrument which is to be prepared. To this end, the method, the reprocessing apparatus and the volume flow determining, which is described more below, can be used.

The volume flow can be determined on the basis of the speed of the gas bubbles.

Such object can be additionally achieved by a volume flow determining module for use in or with a reprocessing apparatus for cleaning and/or disinfecting a medical instrument, wherein the volume flow determining module comprises a fluid line or a portion of a fluid line, a bubble introducing apparatus for introducing gas bubbles into the fluid line or the portion of the fluid line, and a gas bubble speed determining apparatus.

The volume flow determining module can be used in a reprocessing apparatus for cleaning and/or disinfecting a medical instrument. The method can be applied by means of the volume flow determining module.

The gas bubble speed determining apparatus can have a camera for capturing successive images of at least a portion of the fluid line. The fluid line or the portion of the fluid line can be provided with a portion or a part which is transparent. The gas bubble speed determining apparatus can have an illumination apparatus, wherein the illumination apparatus can emit light in the infrared range. The light can be shone into the fluid line substantially parallel or antiparallel to a central axis of the fluid line, such as at a previously indicated angle to the central axis of the fluid line or to the fluid line. In addition, the further preferred measures, which are also already indicated regarding the reprocessing apparatus, can also be provided in the case of the volume flow determining module.

Further features will become evident from the description of embodiments, together with the claims and the appended drawings. Embodiments can fulfill individual features or a combination of several features.

BRIEF DESCRIPTION OF THE DRAWINGS

The embodiments are described below without limiting the general concept of the invention by means of exemplary embodiments with reference to the drawings, wherein reference is expressly made to the drawings regarding all of the details which are not explained in greater detail in the text, wherein.

In the drawings, the same or similar elements and/or parts are, in each case, provided with the same reference numerals so that they are not introduced again in each case.

DETAILED DESCRIPTION

Figure 1:
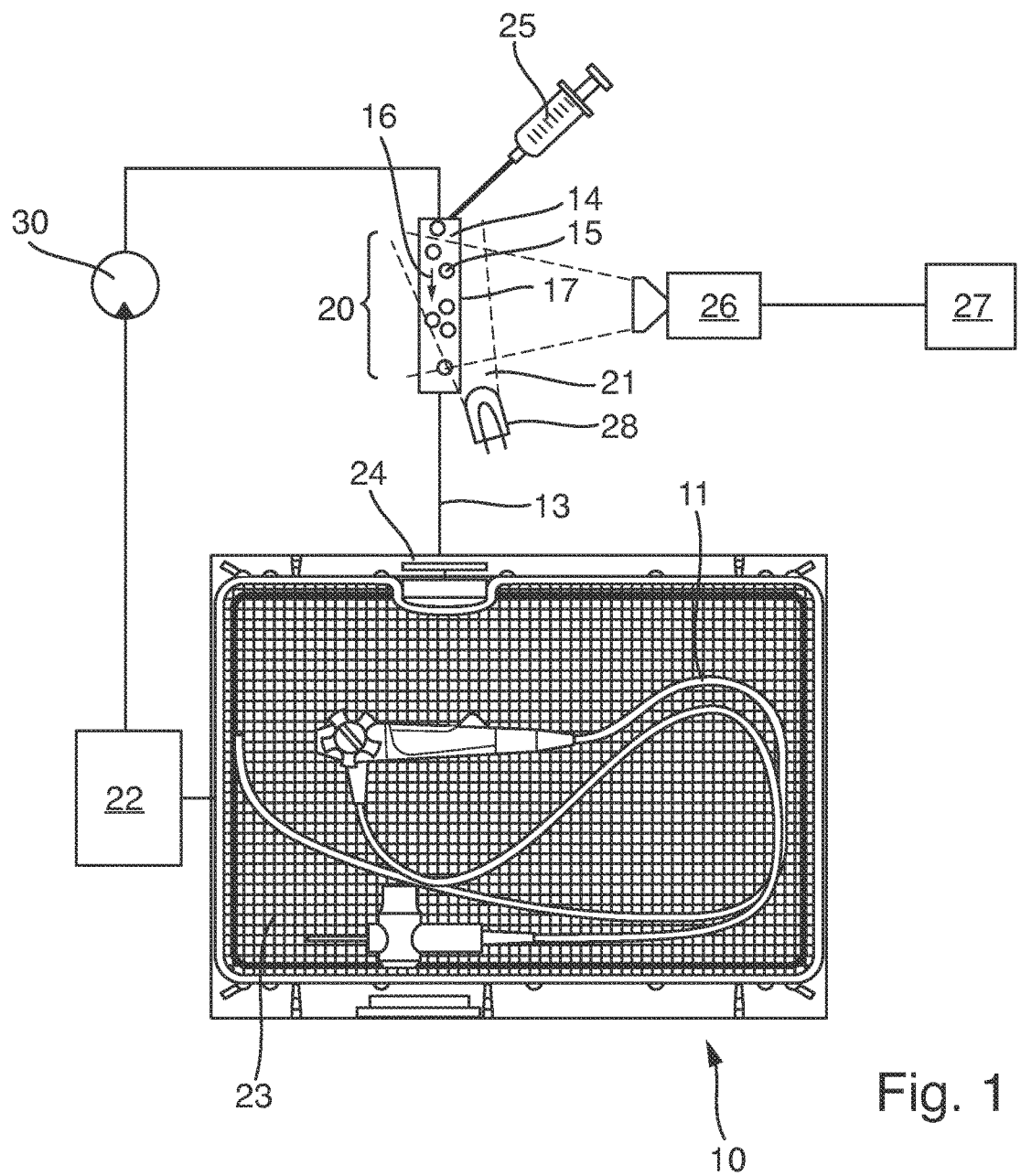
FIG. 1 illustrates a schematic view of a reprocessing apparatus for cleaning and/or disinfecting medical instruments.

FIG. 1 schematically shows a reprocessing apparatus for cleaning and/or disinfecting medical instruments 11. A reprocessing device 10 is provided, which has a basket for receiving an endoscope 11 in a reprocessing space 23. The endoscope 11 comprises one channel or multiple channels, which are not represented in FIG. 1, which is/are to be cleaned or disinfected. The channels are rinsed with a liquid which is supplied by an adapter apparatus 24 via lines which are not represented. An appropriate adapter apparatus or respectively distribution apparatus is represented in WO 2011/149, 539 A1.

The liquid arrives via fluid lines 13, such as in a circuit from a fluid container 22 driven by a pump 30 to the adapter apparatus 24, either partially directly into the reprocessing space 23 and/or via the lines which are not represented into the channels of the endoscope 11 and from the ends of the channels into the reprocessing space 23 and from the reprocessing space 23 back into the fluid container 22. Cleaning of the liquid which is guided in the circuit can also be provided, or alternatively no circuit, but a constant supply of fresh clean liquid can be provided.

Gas bubbles 15 are introduced into the fluid line 13, by way of a bubble introducing apparatus 25 which is schematically represented as a syringe, and indeed into the liquid 14. The liquid 14 continues to move in the flow direction 16 in the fluid line 13. The gas bubbles 15 are captured in a portion 20 by a camera 26 having an image sensor and the speed of the gas bubbles 15 in the portion 20 is determined by evaluating successive images of the camera in a computer system 27. This is explained in even greater detail below. Within the framework of the invention, a computer system 27 can be any apparatus which performs digital calculations, such as a CPU, controller, processor or circuit.

In order to increase the contrast of the gas bubbles 15 in the fluid 14, an illumination apparatus 28 is provided, which substantially shines light, such as infrared light, into the portion 20 or respectively section 20 of the fluid line parallel or antiparallel to the flow direction 16. The light is provided with the reference numeral 21. The dashed lines around the reference numeral 21 indicate the angle of divergence of the rays of the illumination apparatus 28 and corresponding dashed lines from the camera 26 indicate the image section of the camera 26.

The measuring principle is to be explained in greater detail in connection with FIG. 2. The measuring principle for establishing the speed of the gas bubbles 15 or respectively the volume flow establishment method can be based on a particle image velocimetry method.

Figure 2:
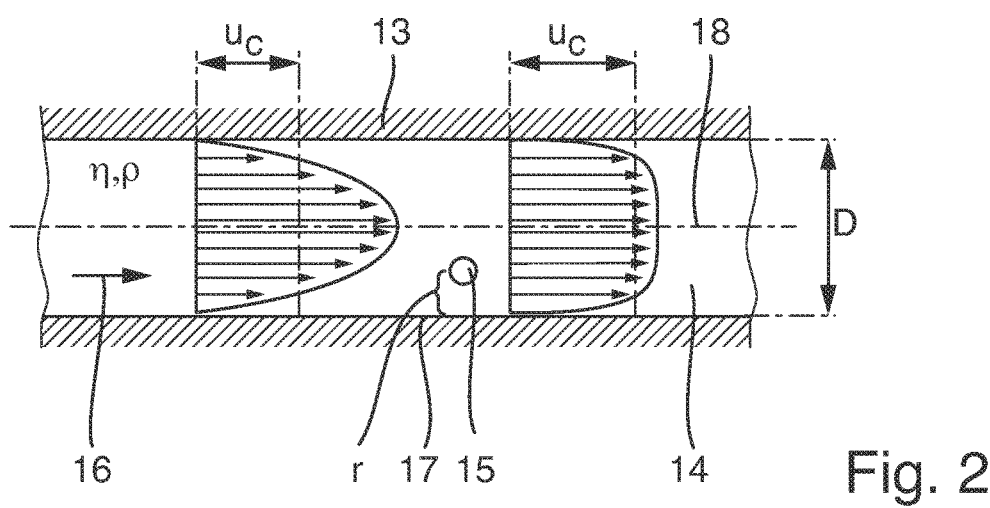
FIG. 2 illustrates a schematic cross-sectional view of a portion of a fluid line, in which possible flow profiles are represented.

FIG. 2 shows a schematic cross-sectional view of a fluid line 13, in which speed profiles of fluids are represented. The fluid line 13 has a wall 17 and a diameter D. A liquid 14 which flows in the flow direction 16 and has a density ρ as well as a viscosity η is provided in the fluid line 13. In addition, a speed profile for a laminar flow is shown on the left in FIG. 2, and a speed profile for a turbulent flow is shown on the right in FIG. 2. The average speed $u_c$ is also represented.

During particle image velocimetry moving objects are captured in a series of images. Due to the movement of the objects or of an object in consecutive images of a series of images, a movement vector as well as the movement speed of the object are established. To this end, visible objects are present in a fluid flow. Gas bubbles or air bubbles are used to this end.

The movement vector of these gas bubbles is determined in order to establish a flow speed. For example, a phase correlation can be used, which has a cross correlation as its basis. This is based on the fact that displaced signals have the same amplitude, but different phases in the Fourier space. In the case of particle image velocimetry, the actual speed is measured at one point in the flow or respectively in the fluid flow and an average flow speed can be calculated therefrom. The average flow speed, with which the volume flow can be calculated, depends on whether the flow is a laminar or a turbulent flow. FIG. 2 is to be considered for this purpose. A basic version of FIG. 2 is extracted from the textbook "Strömungsmechanik—Einführung in die Physik von technischen Strömungen" ["Flow Mechanics—an Introduction to the Physics of Technical Flows"], Vieweg+Teubner 2008.

In the case of a laminar flow, the flow is layered since the movement speed of the fluid particles only lies in the direction of the pipe axis or respectively the fluid line axis. The fluid particles or respectively gas bubbles therefore have a fixed position relative to the central axis 18 of the fluid line 13. The maximum speed lies centrally in the pipe on the axis 18 and the lowest speed lies on the wall 17 (see left side of FIG. 2).

In the case of turbulent flows there is a constant turbulence of the fluid in the flow cross-section such that the same flow speed substantially prevails over the entire cross-section. This corresponds to the average flow speed in one approximation (see right side of FIG. 2). In order to distinguish between a laminar and a turbulent flow, the Reynolds number is cited. If the Reynolds number is above the limit of 2,300, the flow is turbulent. If the Reynolds number is lower, the flow is laminar. At low flow speeds, a laminar flow is consequently to be expected and at high flow speeds, a turbulent flow is to be expected. The volume flow can be determined over the cross-sectional area of the fluid line 13 and the determined average speed $u_c$. A typical boundary volume flow, in which the transition takes place from a laminar to a turbulent flow, is approximately 870 ml/min in the case of fluid lines which are used for cleaning and/or disinfecting medical instruments such as endoscopes. In the case of the usual medical instruments used, the boundary volume flow is 400 ml/min to 1000 ml/min, such as 600 ml/min to 900 ml/min.

The flow measurement or respectively the measurement of the speed of the gas bubbles can be performed in the vicinity of the wall 17. The distance of the measurement cab be greater than or equal to $R/2^{1/2}$, wherein R is the radius of the fluid line 13 or is respectively half the diameter D.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

10 Reprocessing device
11 Endoscope

13 Fluid line
14 Liquid
15 Gas bubble
16 Flow direction
17 Wall
18 Central axis
20 Section
21 Light
22 Fluid container
23 Reprocessing space
24 Adapter apparatus
25 Bubble introducing apparatus
26 Camera
27 Computer system
28 Illumination apparatus
30 Pump
u Speed
$u_c$ Average speed
D Diameter
R Radius
r Distance from the wall
η Viscosity
ρ Density

What is claimed is:

1. A reprocessing apparatus for cleaning and/or disinfecting a medical instrument, the reprocessing apparatus comprising:
    a fluid container for a reprocessing fluid; and
    a reprocessing device, wherein the reprocessing device comprises:
        a reprocessing space in which the medical instrument is introduced for reprocessing;
        a fluid line for connection to at least one channel of the medical instrument, wherein the fluid line is configured to transport the reprocessing fluid to the at least one channel;
        a pump configured to introduce gas bubbles into the fluid line;
        a gas bubble speed determining apparatus comprising a camera, the camera being configured to capture successive images of at least a portion of the gas bubbles in the fluid line; and
        a controller comprising hardware, the controller being configured to determine a speed of the gas bubbles in the fluid line from the successive images.

2. The reprocessing apparatus according to claim 1, wherein at least a portion of the fluid line is transparent.

3. The reprocessing apparatus according to claim 1, wherein the gas bubble speed determining apparatus further comprises an illumination apparatus for illuminating the gas bubbles with light.

4. The reprocessing apparatus according to claim 3, wherein the illumination apparatus emits light in an infrared range.

5. The reprocessing apparatus according to claim 3, wherein the illumination apparatus directs the light into the fluid line one of approximately parallel or antiparallel to a central axis of the fluid line.

6. The reprocessing apparatus according to claim 2, wherein the portion of the fluid line that is transparent comprises at least one region which is $\geq R/2^{1/2}$ distant from a central axis of the fluid line, wherein R is one of a radius of the fluid line or a distance of the central axis from a wall of the fluid line.

7. The reprocessing apparatus according to claim 1, wherein the gas bubble speed determining apparatus further comprises a computer configured to perform a fast Fourier transform of the successively captured images.

8. The reprocessing apparatus according to claim 7, wherein a movement vector of the gas bubbles is established by a phase correlation.

9. A volume flow determining module for use with a reprocessing apparatus for cleaning and/or disinfecting a medical instrument, the volume flow determining module comprising:
    a fluid line;
    a pump configured to introduce gas bubbles into at least a portion of the fluid line;
    a camera for capturing successive images of at least a portion of the gas bubbles in the fluid line; and
    a controller comprising hardware, the controller being configured to determine a speed of the gas bubbles in the fluid line from the successive images.

* * * * *